United States Patent

Shiokawa et al.

[11] Patent Number: 5,827,845
[45] Date of Patent: Oct. 27, 1998

[54] CEPHALOSPORIN DERIVATIVE

[75] Inventors: Sohjiro Shiokawa; Kunio Atsumi; Katsuyoshi Iwamatsu; Atsushi Tamura; Seiji Shibahara, all of Yokohama, Japan

[73] Assignee: Meiji Seika Kaisha, Ltd., Tokyo, Japan

[21] Appl. No.: 617,870

[22] PCT Filed: Sep. 29, 1994

[86] PCT No.: PCT/JP94/01618

§ 371 Date: Jul. 31, 1996

§ 102(e) Date: Jul. 31, 1996

[87] PCT Pub. No.: WO95/09171

PCT Pub. Date: Apr. 6, 1995

[30] Foreign Application Priority Data

Sep. 29, 1993 [JP] Japan .................................. 5-243324

[51] Int. Cl.$^6$ ........................ C07D 501/56; A61K 31/545
[52] U.S. Cl. ........................................... 514/206; 540/227
[58] Field of Search .............................. 540/227; 514/206

[56] References Cited

FOREIGN PATENT DOCUMENTS 62-205088  9/1987  Japan .
3-264590  11/1991  Japan .

*Primary Examiner*—John M. Ford
*Attorney, Agent, or Firm*—Larson & Taylor

[57] ABSTRACT

A cephalosporin derivative which has a substituted or unsubstituted 2-(5-thiazolyl)vinyl group at the 3-position and is represented by the following formula (I)

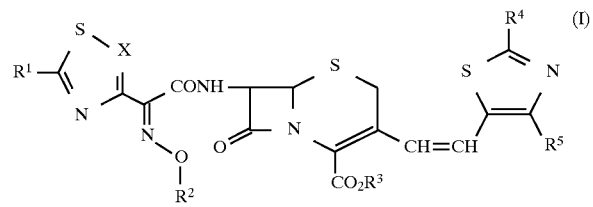

wherein X is CH or N, $R^1$ is an amino group or a protected amino group, $R^2$ is a hydrogen atom or a hydroxyimino-protecting group, $R^3$ is a hydrogen atom, a salt-forming cation or a carboxyl-protecting group, $R^4$ is a hydrogen atom, and $R^5$ is a hydrogen atom, a lower alkyl group, a halo-(lower)alkyl group or a halogen atom, is now synthetised as a cephem compound which exhibits excellent antibacterial activities and is useful as a therapeutic agent for various bacterial infections.

8 Claims, No Drawings

CEPHALOSPORIN DERIVATIVE

This is a 371 of PCT/JP94/01618 filed Sep. 29, 1994

TECHNICAL FIELD

This invention relates to novel cephem compounds having useful antibacterial activities, more particularly cephalosporin derivatives and pharmaceutically acceptable salts or esters thereof.

BACKGROUND ART

Antibiotics of cephalosporin type have excellent antibacterial activities against bacteria and exhibit low toxicity to mammals, and hence they are a medicine which is very much effective in therapeutic treatments of bacterial infections in mammals.

A variety of semi-synthetic cephalosporin derivatives having a wide range of antibacterial activities against gram-positive bacteria and gram-negative bacteria are already synthetised and available commercially, and they are now used clinically as a therapeutic agent for various bacterial infections. Among the known cephalosporin derivatives, however, such cephalosporin derivatives which can exhibit a high antibacterial activity against *Pseudomonas aeruginosa* and Proteus species are few. Many of the known cephalosporin derivatives have further such drawback that they are unstable to the β-lactamase as produced by some resistant strains of bacteria and exhibit poor antibacterial activities against various resistant strains of bacteria which have now been a target of the clinical treatments of the bacterial infections. They can also have another certain drawbacks. Besides, many of the existing antibacterial compounds of the cephem series have been exploited mainly for use as injections and thus they can have such drawback that when they are orally administered, their rate of absorption in the living body is poor so that they do not exhibit a sufficiently high efficacy in the therapeutic treatments of bacterial infections.

In recent years, researches and exploitions have been made of such cephalosporin derivatives having amino-thiazolylacetyl group at the 7-position of the cephem ring since many of said cephalosporin derivatives can exhibit high antibacterial activities and a stability to β-lactamase.

For example, the known cephem compounds having the aminothiazolylacetyl group at the 7-position and a β-substituted or unsubstituted vinyl group at the 3-position of the cephem ring include Cefixime having the following formula (A)

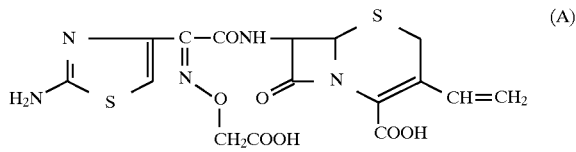

and Cefdinir having the following formula (B)

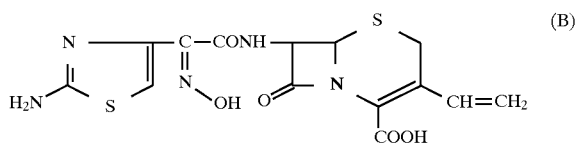

Also, there is known a cephem compound (syn-isomer) represented by the following general formula (C)

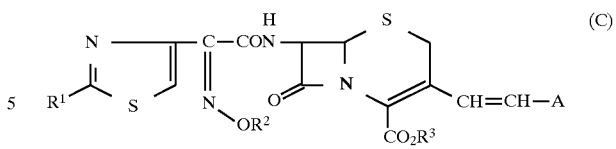

wherein $R^1$ is an amino group or a protected amino group, $R^2$ is a lower alkyl group, carboxymethyl group or a protected carboxymethyl group, $R^3$ is a hydrogen atom, a salt-forming cation or a carboxyl-protecting group, and A stands for phenyl group, a lower alkyl-phenyl group, a lower alkoxy-phenyl group, or a halo-phenyl group, or furyl group, nitro-furyl group, or a halo-furyl group or thiazolyl group, a lower alkyl-thiazolyl group or a halo-thiazolyl group, or a 3-lower alkyl-thiazolio group which may further bear one lower alkyl substituent at a position other than the 3-position of the thiazolyl ring and has an anionic counter-ion associated with the quarternary nitrogen atom at the 3-position of the thiazolio group, or a salt or an ester of said cephem compound (see Japanese patent publication No. Hei-3-64503, European patent No. 0175610 and U.S. Pat. No. 4,839,350). One example of the cephem compound of the general formula (C) is 7-[2-methoxyimino-2-(2-aminothiazol-4-yl)acetamido]-3-[2-(4-methylthiazol-5-yl)vinyl]-3-cephem-4-carboxylic acid (syn-isomer, cis-isomer), which is abbreviated as ME1206 compound hereinafter. Pivaloyloxymethyl ester of this ME1206 compound, which is abbreviated as ME1207 compound hereinafter, is known under a common name of "Cefditoren pivoxil".

Furthermore, syn-isomer of a cephem compound represented by the following general formula (D)

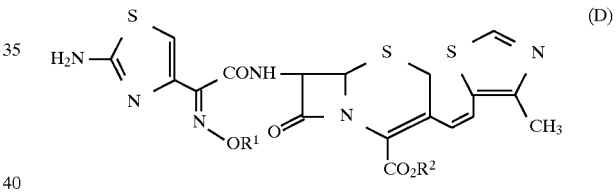

wherein $R^1$ is a lower ($C_1$–$C_6$)alkyl group, and $R^2$ is an ester-forming group cleavable by hydrolysis in vivo, and wherein the 4-methylthiazolyl group and the cephem ring are in "cis"-position around the carbon-carbon double bond of the substituted vinyl group at the 3-position of the cephem compound is known to have a high absorption in the living body when it is orally administerd (see U.S. Pat. No. 4,918,068 and European patent No. 0236231).

We, the present inventors, have continued to make researches in an attempt to provide such new cephalosporin derivatives having improved antibacterial activities over those of Cefixime, Cefdinir and ME1206 compound and also having other favorable properties. As a result, we have succeeded in synthetising a new cephalosporin derivative which has a β-(4-substituted or unsubstituted-thiazol-5-yl) vinyl group at the 3-position of the cephem ring, has 2-(2-aminothiazol-4-yl)acetamido group or 2-(2-amino-1,2,4-thiadiazol-3-yl)acetamido group and also has an optionally protected hydroxyimino group introduced as a substituent at the α-position of the acyl group present at the 7-position of the cephem ring, and which is collectively represented by a general formula (I) given hereinafter.

Further, the present inventors have now found that the new cephalosporin-type compounds represented by the general formula (I) given hereinafter can exhibit a very much wide range of antibacterial spectrum, that these new cephalosporins exhibit high antibacterial activities against gram-positive bacteria, gram-negative bacteria and various resistant strains of the bacteria, and that these new cephalosporins have enhanced anti-bacterial activities over those of Cefixime, Cefdinir and ME1206 compound and especially can exhibit very much high antibacterial activities not only against *Staphylococcus aureus* but also against *Enterococcus faecalis*. On the basis of these findings, the present inventors have accomplished the present invention.

DISCLOSURE OF THE INVENTION

Thus, according to a first aspect of this invention, there is provided syn-isomer of a cephem compound represented by the following general formula (I)

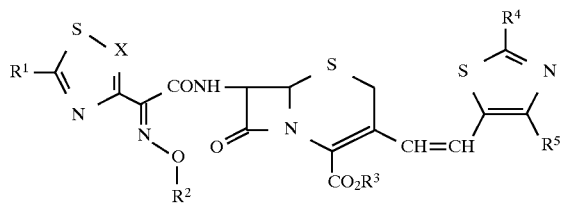

wherein X is CH or N, $R^1$ is an amino group or a protected amino group, $R^2$ is a hydrogen atom or a hydroxyimino-protecting group, $R^3$ is a hydrogen atom, a salt-forming cation or a carboxyl-protecting group, $R^4$ is a hydrogen atom, and $R^5$ is a hydrogen atom, a lower alkyl group, a halo-(lower)alkyl group or a halogen atom, or a pharmaceutically acceptable salt or ester of said syn-isomer.

In the compound of the formula (I) according to this invention, the thiazolyl group attached to the β-position of the substituted vinyl group at the 3-position of the cephem ring may be either thiazol-5-yl group having no substituent on the thiazole ring, or a 4-lower alkyl-thiazol-5-yl group, a 4-halo-thiazol-5-yl group or a 4-halo-(lower)alkyl-thiazol-5-yl group. The compound of the formula (I) according to this invention include (E)-isomer (namely, trans-isomer) and (Z)-isomer (namely, cis-isomer), depending on the relative positions of the substituent and the hydrogen atom attached to the substituted vinyl group at the 3-position of the cephem ring. This invention includes the (E)-isomer or the (Z)-isomer of the compound of the formula (I), or a mixture thereof.

Some of the various terms used in this specification hereinbefore and hereinafter have such definitions and meanings as detailed below, and appropriate examples as encompassed by these terms are described below in details.

The term "lower" used in the term "lower alkyl group" or the term "lower alkoxy group" means such one containing 1 to 6 carbon atoms, unless stated otherwise. In the compound of the formula (I) where $R^1$ means a protected amino group, the amino-protecting group is an ordinary amino-protecting group which is readily cleavable by hydrolysis or hydrogenolysis and which may be a lower alkoxycarbonyl group such as tert-butoxycarbonyl group, or formyl group or a halo-lower alkanoyl group such as chloroacetyl group, or trityl group. When $R^2$ means a hydroxyimino-protecting group, this is such a hydroxymimino-protecting group which is readily cleavable by acid hydrolysis and which may be trityl group or a lower alkoxy-lower alkyl group such as methoxymethyl group, or a lower alkoxy-lower alkoxy-lower alkyl group such as methoxyethoxymethyl group.

When $R^3$ means a salt-forming cation, this may be such cation which forms an alkali metal salt, an alkaline earth metal salt, ammonium salt or the like. When $R^3$ means a carboxyl-protecting group, such carboxyl-protecting group includes a carboxyl-protecting group which is conventionally employed to protect the 4-carboxyl group of cephalosporins and which may be allyl group, a lower alkoxymethyl group, a lower alkylthiomethyl group, a lower alkanoyloxymethyl group or a lower alkoxy-substituted benzyl group such as p-methoxybenzyl group.

When the compound of the formula (I) according to this invention is in the form of an ester thereof, $R^3$ may be a metabolically unstable ester-forming group which is hydrolyzable and cleavable in vivo and which may be a lower alkoxycarbonyloxyalkyl group, a lower alkylcarbonyloxyalkyl group or a (2-oxo-1,3-dioxolen-4-yl)-methyl group optionally bearing a substituent such as a 5-lower alkyl group, or the like. When $R^5$ means a halo-(lower)alkyl group or a halogen atom, the halo substituent or the halogen atom may be fluorine atom, chlorine atom, bromine atom or iodine atom but preferably be fluorine atom or chlorine atom.

The cephem compound of the formula (I) according to the first aspect of this invention or a salt or an ester thereof includes a cephem compound of formula (Ia), a cephem compound of formula (Ib) and a cephem compound of formula (Ic) as indicated below, as well as salts or esters of them.

(1) Syn-isomer of the cephem compound represented by the following formula (Ia)

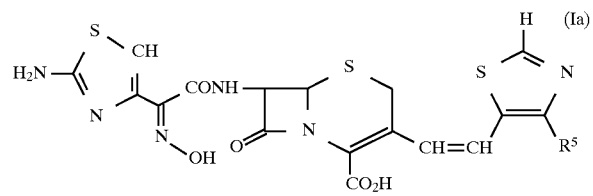

Wherein $R^5$ stands for a hydrogen atom, a lower alkyl group, a halo-(lower)alkyl group or a halogen atom, or a pharmaceutically acceptable salt or ester at the 4-carboxyl group of said syn-isomer.

(2) Syn-isomer of the cephem compound represented by the following formula (Ib)

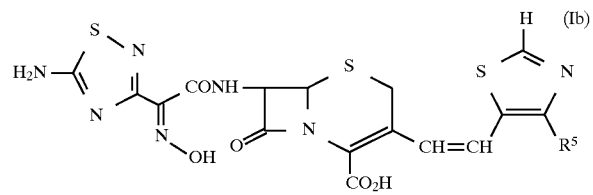

wherein $R^5$ stands for a hydrogen atom, a lower alkyl group, a halo-(lower)alkyl group or a halogen atom, or a pharmaceutically acceptable salt or ester at the 4-carboxyl group of said syn-isomer.

(3) Syn-isomer of the cephem compound of which the functional groups have been protected and which is represented by the following formula (Ic)

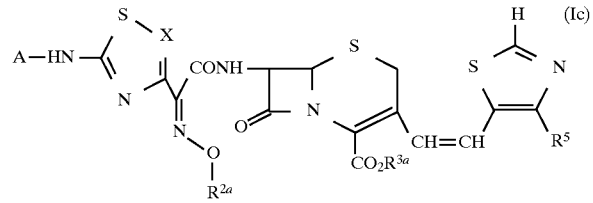

wherein X is CH or N, A is such an amino-protecting group which is easily cleavable by acid hydrolysis or hydrogenolysis and which is selected from an alkoxycarbonyl group, formyl group, a halo-(lower)alkanoyl group and trityl group, $R^{2a}$ is such a hydroxyimino-protecting group which is easily cleavable by acid hydrolysis and which is selected from trityl group, a lower-alkoxy-lower alkyl group and a lower-alkoxy-lower alkoxy-lower alkyl group. $R^{3a}$ is a carboxyl-protecting group selected from an aryl group, a lower alkyl group, a lower alkoxymethyl group, a lower alkylthiomethyl group, a lower alkanoyloxymethyl group and a lower alkoxy-substituted benzyl group, and $R^5$ is a hydrogen atom, a lower alkyl group, a halo-(lower)alkyl group or a halogen atom.

Particular examples of the cephem compound of the formula (Ia) or a salt or an ester thereof includes:

7-[2-hydroxyimino-2-(2-aminothiazol-4-yl)acetamido]-3-[2-(4-chlorothiazol-5-yl)vinyl]-3-cephem-4-carboxylic acid (syn-isomer)(cis-isomer);

7-[2-hydroxyimino-2-(2-aminothiazol-4-yl)acetamido]-3-[2-(4-trifluoromethylthiazol-5-yl)vinyl]-3-cephem-4-carboxylic acid (syn-isomer)(cis-isomer);

7-[2-hydroxyimino-2-(2-aminothiazol-4-yl)acetamido]-3-[2-(4-methylthiazol-5-yl)vinyl]-3-cephem-4-carboxylic acid (syn-isomer)(cis-isomer);

7-[2-hydroxyimino-2-(2-aminothiazol-4-yl)acetamido]-3-[2-(thiazol-5-yl)vinyl]-3-cephem-4-carboxylic acid (synisomer)(cis-isomer);

7-[2-hydroxyimino-2-(2-aminothiazol-4-yl) acetamido]-3-[2-(thiazol-5-yl)vinyl]-3-cephem-4-carboxylic acid (synisomer)(trans-isomer) or a mixture of the cis-isomer and trans-isomer; or sodium salt, pivaloyloxymethyl ester, acetoxymethyl ester, 1-acetoxyethyl ester, 1-(ethoxycarbonyloxy)ethyl ester, (2-oxo-1,3-dioxolen-4-yl)methyl ester or (5-methyl-2-oxo-1,3-dioxolen-4-yl)methyl ester of the above-mentioned cephem compounds.

Particular examples of the cephem compound of the formula (Ib) or a salt or an ester thereof includes:

7-[2-hydroxyimino-2-(5-amino-1,2,4-thiadiazol-3-yl) acetamido]-3-[2-(4-chlorothiazol-5-yl)vinyl]-3-cephem-4-carboxylic acid (syn-isomer)(cis-isomer);

7-[2-hydroxyimino-2-(5-amino-1,2,4-thiadiazol-3-yl) acetamido]-3-[2-(4-trifluoromethylthiazol-5-yl)vinyl]-3-cephem-4-carboxylic acid (syn-isomer)(cis-isomer);

7-[2-hydroxyimino-2-(5-amino-1,2,4-thiadiazol-3-yl) acetamido]-3-[2-(4-methylthiazol-5-yl)vinyl]-3-cephem-4-carboxylic acid (syn-isomer)(cis-isomer);

7-[2-hydroxyimino-2-(5-amino-1,2,4-thiadiazol-3-yl)-acetamido]-3-[2-(thiazol-5-yl)vinyl]-3-cephem-4-carboxylic acid (syn-isomer)(cis-isomer); or sodium salt, pivaloyloxymethyl ester, acetoxymethyl ester, 1-acetoxyethyl ester, 1-(ethoxycarbonyloxy)ethyl ester, (2-oxo-1,3-dioxolen-4-yl)methyl ester or (5-methyl-2-oxo-1,3-dioxolen-4-yl)methyl ester of the above-mentioned cephem compounds.

Particular examples of the cephem compound of the formula (Ic) includes:

p-methoxybenzyl 7-[2-trityloxyimino-2-(2-tritylaminothiazol-4-yl)acetamido]-3-[2-(4-chlorothiazol-5-yl)-vinyl]-3-cephem-4-carboxylate(syn-isomer)(cis-isomer);

p-methoxybenzyl 7-[2-trityloxyimino-2-(2-tritylaminothiazol-4-yl)acetamido]-3-[2-(4-trifluoromethylthiazol-5-yl)vinyl]-3-cephem-4-carboxylate (syn-isomer)(cis-isomer);

p-methoxybenzyl 7-[2-trityloxyimino-2-(2-tritylaminothiazol-4-yl)acetamido]-3-[2-(4-methylthiazol-5-yl)-vinyl]-3-cephem-4-carboxylate (syn-isomer)(cis-isomer);

p-methoxybenzyl 7-[2-trityloxyimino-2-(2-tritylaminothiazol-4-yl)acetamido]-3-[2-(thiazol-5-yl)vinyl]-3-cephem-4-carboxylate (syn-isomer)(cis isomer or trans-isomer or a mixture of cis-isomer and trans-isomer);

p-methoxybenzyl 7-[2-trityloxyimino-2-(5-trityl-amino-1,2,4-thiadiazol-3-yl)acetamido]-3-[2-(4-methylthiazol-5-yl)vinyl]-3-cephem-4-carboxylate (syn-isomer)(cis-isomer); or p-methoxybenzyl 7-[2-trityloxyimino-2-(5-trityl-amino-1,2,4-thiadiazol-3-yl)acetamido]-3-[2-(4-trifluoromethylthiazol-5-yl)vinyl]-3-cephem-4-carboxylate (syn-isomer)(cis-isomer), and others.

The cephem compound of the general formula (I) according to this invention, including the compound of the formula (Ia) and the compound of the formula (Ib), may be in the form of a pharmaceutically acceptable salt thereof. Appropriate examples of the pharmaceutically acceptable salt are such usual, pharmaceutically acceptable and non-toxic salts which include a metal salt, for example, a salt with an alkali metal such as sodium and potassium; an alkaline earth metal such as calcium and magnesium; a salt with ammonium; a salt with a pharmaceutically acceptable organic base such as triethylamine, trimethylamine, pyridine, picoline, dicyclohexylamine and N,N'-dibenzyl ethylenediamine; and a salt with a pharmaceutically acceptable organic acid such as acetic acid, trifluoroacetic acid, maleic acid, tartaric acid, methanesulfonic acid, benzenesulfonic acid, formic acid and toluenesulfonic acid; and a salt with an amino acid such as arginine, aspartic acid and glutamic acid.

The cephalosporin derivative of the general formula (I) according to this invention has a high anti-bacterial activity to a variety of pathogenic bacteria. This cephalosporin derivative encompasses some examples of the cephalosporin which can exhibit a considerably high absorption upon their oral administration and which also have such properties of giving and maintaining a high concentration in blood after the administration. Next, the advantageous properties of the compounds of this invention are illustrated by the following Test Examples with reference to some representative cephem compounds.

TEST EXAMPLE 1

In this Example, it is demonstrated that among the compounds of the general formula (I) according to this invention, some representative examples thereof have high antibacterial activities as shown by their minimum growth inhibitory concentrations (MIC., $\mu$g/ml) against various bacteria, which were determined by a usual serial dilution method. The determination of MIC. was conducted by inoculating the test microorganism to an incubation medium N for sensitive disc (a product of Nissui Seiyaku Co., Japan), effecting the incubation at 35° C. for 18–20 hours and then estimating the growth of the bacteria. The compounds tested were the sodium salts of Compound A to Compound F indicated below:

(1) Compound A:

7-[2-Hydroxyimino-2-(2-aminothiazol-4-yl)acet-amido]-3-[2-(4-chlorothiazol-5-yl)vinyl]-3-cephem-4-carboxylic acid (syn-isomer, cis-isomer)(see Example 2 given hereinafter)

(2) Compound B:

7-[2-Hydroxyimino-2-(2-aminothiazol-4-yl)acet-amido]-3-[2-(4-trifluoromethylthiazol-5-yl)vinyl]-3-cephem-4-carboxylic acid (syn-isomer, cis-isomer)(see Example 5 given hereinafter)

(3) Compound C:
7-[2-Hydroxyimino-2-(2-aminothiazol-4-yl)acet-amido]-3-[2-(4-methylthiazol-5-yl)vinyl]-3-cephem-4-carboxylic acid (syn-isomer, cis-isomer) (see Example 8 given hereinafter)

(4) Compound D:
7-[2-Hydroxyimino-2-(2-aminothiazol-4-yl)acet-amido]-3-[2-(thiazol-5-yl)vinyl]-3-cephem-4-carboxylic acid(syn-isomer, cis-isomer) (see Example 11 given hereinafter)

(5) Compound E:
7-[2-Hydroxyimino-2-(2-aminothiazol-4-yl)acet-amido]-3-[2-(thiazol-5-yl)vinyl]-3-cephem-4-carboxylic acid (syn-isomer, trans-isomer) (see Example 13 given hereinafter)

(6) Compound F
7-[2-Hydroxyimino-2-(5-amino-1,2,4-thiadiazol-3-yl) acetamido]-3-[2-(4-methylthiazol-5-yl)vinyl]-3-cephem-4-carboxylic acid (syn-isomer, cis-isomer) (see Example 16 given hereinafter)

The determined values of the minimum growth inhibitory concentrations (MIC., μg/ml) of the above-mentioned Compound A to Compound F are shown in Table 1 below. For the comparison purpose, the values similarly determined of MIC. (μg/mg) of ME1206 compound (sodium salt), Cefdinir (sodium salt) (abbreviated as CFDN) and Cefixime (sodium salt) (abbreviated as CFIX) are also shown in Table 1.

converted into the form of the corresponding free acid. Quantitative measurement was made of the total quantity of the compound of this invention which was excreted into the urine as collected during the period of 0 to 4 hours after the administration of the test compound, and evaluation was made of rate (%) of recovery of the compound in the urine.

Procedure of the quantitative measurement: The quantitative measurement of the test compound was conducted by assaying the urine according to a high performance liquid chromatography (Column: Licrosorb RP18, 4φ×150 mm; detected at 270 nm by a UV-detector).

The test results obtained (as an average of the results obtained for three mice) are shown in Table 2 below.

TABLE 2

| Test compound (as pivaloyl-oxymetyl ester | Rate (%) of recovery of the compound in urine |
|---|---|
| Compound C | 4.6 |
| Compound D | 2.0 |

TEST EXAMPLE 3

In this Example, it is demonstrated by the undermentioned test procedure that the aforesaid Compounds A,

TABLE 1

| | Minimum growth inhibition concentrations (μg/ml) | | | | | | | | |
|---|---|---|---|---|---|---|---|---|---|
| Test microorganisms | Compound A | Compound B | Compound C | Compound D | Compound E | Compound F | ME1206 (comparative) | CFDN (comparative) | CFIX (comparative) |
| *Staphylococcus aureus* 209P JC-1 | 0.10 | 0.39 | 0.20 | 0.10 | 0.20 | 0.39 | 0.39 | 0.20 | 12.5 |
| *Staphylococcus aureus* M133* | 6.25 | 6.25 | 6.25 | 3.13 | 6.25 | 3.13 | 25 | 6.25 | 100 |
| *Staphylococcus aureus* M126* | 25 | 25 | 25 | 25 | 25 | 50 | 100 | >100 | >100 |
| *Enterococcus hirae* ATCC 8043 | 12.5 | 6.25 | 6.25 | 12.5 | 25 | 25 | 50 | 50 | >100 |
| *Enterococcus faecalis* W-73 | 6.25 | 12.5 | 12.5 | 1.56 | 3.13 | 25 | 100 | 25 | >100 |
| *Escherichia coli* 255 | 12.5 | 6.25 | 12.5 | 6.25 | 6.25 | 25 | 12.5 | 50 | >100 |
| *Escherichia coli* GN 206 | 1.56 | 1.56 | 3.13 | 1.56 | 0.78 | 6.25 | 0.78 | 25 | 50 |
| *Morganella morganii* 1510 | 12.5 | 1.56 | 1.56 | 12.5 | 6.25 | 25 | 25 | 25 | 50 |
| *Enterobacter cloacae* G-0008 | 1.56 | 1.56 | 0.78 | 0.78 | 0.78 | 1.56 | 1.56 | 6.25 | 0.78 |
| *Serratia marcescens* No. 1 | 1.56 | 1.56 | 1.56 | 0.78 | 0.78 | 3.13 | 0.39 | 25 | 0.78 |

Note: mark (*) denotes methicillin-resistant *Staphylococcus aureus* (MRSA)

TEST EXAMPLE 2

Pivaloyloxymethyl ester of Compound C (the compound obtained in Example 9 given hereinafter) or pivaloyloxymethyl ester of Compound D (the compound obtained in Example 12 given hereinafter) was used as a test compound and administered orally to mice (ICR strain, male, 4 week-aged, 3 mice per group) at a dosage of 0.5 mg per mouse. The method of administration comprised orally administrating a suspension of the test compound suspended in an aqueous solution of 2% carboxymethyl-cellulose (CMC).

Then, all the test compounds (in the ester form), after the administration, were absorbed into the mouse body through the digestive tracts of mouse, and the ester-forming group on the 4-carboxyl group of each test compound was readily cleaved therefrom in vivo so that the test compound was B, C, D, E and F which are representative examples of the compounds according to this invention are capable of maintaining a high concentration in blood when they are injected subcutaneously.

The test procedure used was as follows: Thus, to mice of Jcl;ICR strain (4 week-aged, male) each was administered subcutaneously an aqueous solution containing 2.5 mg/ml of a test compound dissolved in distilled water sterilized for injections, in such a way that 0.2 ml of said aqueous solution (corresponding to a dosage of the test compound of 0.5 mg per mouse) was injected to one mouse. At the time-points of 5, 15, 30, 60 and 120 minutes after the administration, the blood samples were collected from the armpit of mouse. The blood samples so collected were each allowed to stand for about 2 hours at room temperature and then centrifuged for 10 minutes in a centrifugal separator to recover the serum.

The serum obtained was mixed well with an equal volume of methanol added thereto, and the resulting mixture was centrifuged at 12,000 rpm. for 3 minutes. The supernatant obtained was passed through a filter (Sumplep LCR-13-LH) to obtain the serum sample to be assayed by a high performance liquid chromatography (HPLC). This serum sample was assayed by HPLC to measure quantitatively the concentration of the test compound in the serum.

For each test compound, its half-life value in blood and its AUC (Area under the plasma concentration-time curve), which are the pharmacokinetic parameters, were evaluated according to the method of Gauss-Newton.

For the comparison purpose, the ME1206 compound was also tested in the same manner as above. The test results obtained are shown in Table 3 below.

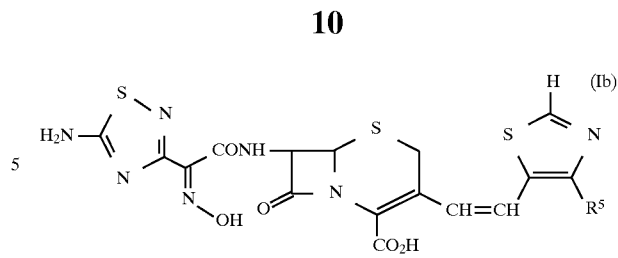

wherein $R^5$ is a hydrogen atom, a lower alkyl group, a halo-(lower)-alkyl group or a halogen atom, or a pharmaceutically acceptable salt or ester at the 4-carboxyl group or said syn-isomer, in association with a pharmaceutically acceptable solid or liquid carrier.

The antibacterial composition according to the second aspect of this invention may be administered in the form of

TABLE 3

| Item of measurement | Test compound (as a sodium salt form) | | | | | | |
|---|---|---|---|---|---|---|---|
| | Compound A | Compound B | Compound C | Compound C | Compound E | Compound F | ME1206 (Comparative) |
| AUC ($\mu$g · hr/ml) | 210.8 | 148.9 | 249.1 | 315.5 | 253.4 | 163.4 | 183.6 |
| Half-life value (hr.) | 1.1 | 0.7 | 1.4 | 1.7 | 1.1 | 0.9 | 1.1 |

Among the cephem compounds of the general formula (I) according to the first aspect of this invention, the such cephem compounds from which the protecting groups on the functional groups of the cephem compounds have been cleaved, that is, the cephem compounds of the above formula (Ia) or formula (Ib) or their pharmaceutically acceptable salts or esters may be formulated into an antibacterial composition comprising the cephem compound or the salt or ester thereof as the active ingredient, in association with an organic or inorganic, solid or liquid carrier suitable for oral administration or non-oral administration or external applications, when said cephem compound is to be administered for the purpose of treating therapeutically bacterial infections.

This antibacterial composition may be prepared in the form of any conventional formulations, which include capsules, tablets, ointments, suppossitories, solutions, suspensions, emulsions and so on. If necessary, the above formulation may further contain a supplementary agent, stabilizer, wetting agent or emulsifier, or buffering agent, or any of other conventional additives.

According to a second aspect of this invention, therefore, there is provided an antibacterial composition, characterized in that the composition comprises as active ingredient at least one of the syn-isomer of a cephem compound represented by the following formula (Ia)

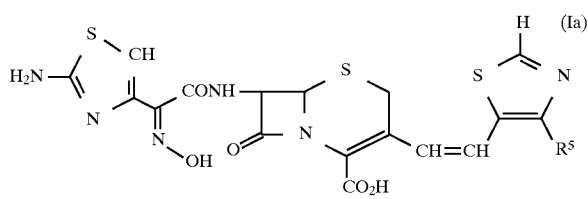

wherein $R^5$ is a hydrogen atom, a lower alkyl group, a halo-(lower)-alkyl group or a halogen atom, or a pharmaceutically acceptable salt or ester at the 4-carboxyl group of said syn-isomer, and the syn-isomer of a cephem compound represented by the following formula (Ib)

a formulation such as injections, orally administrable preparations, suppositories or the like. The excipient or carrier present in the composition may be chosen from the pharmaceutically acceptable ones, and the sort of the excipient or carrier varies depending on the route of administration and the method of administration. For instance, as a liquid carrier may be used water, ethanol, or animal and vegetable oils such as soybean oil, sesami oil, or mineral oil or synthetic oil, and so on. As a solid carrier may be used a sugar such as maltose and sucrose; an amino acid such as lysine; a cellulose derivative such as hydroxypropylcellulose and the like; a polysaccharide such as cyclodextrins; and an organic acid salt such as magnesium stearate, and the like.

When the antibacterial composition is formulated into an injection, in general, the carrier may desirably be physiological saline, various buffered solutions, aqueous solutions of a sugar such as glucose, inositol, mannitol and the like, or a glycol such as ethylene glycol, polyethylene glycol and the like. Further, the anti-bacterial composition may also be formulated into a lyophilised preparation in association with an excipient which may be a sugar such as inositol, mannitol, glucose, mannose, maltose, sucrose and the like, or an amino acid such as phenylalanine and the like. Upon administration, the lyophilised preparation may be dissolved into a solvent suitable for the injection, for example, a liquid available for intravenous injection, which may be sterile water, physiological saline, aqueous solution of glucose, solution of electrolytes and aqueous solution of amino acids.

The proportion of the cephem compound of formula (Ia) or formula (Ib) present in the composition formulated as above may vary according to the type of the formulation but usually may be 0.1 to 99% by weight, preferably 1 to 90% by weight of the composition. For instance, an injectable solution may normally contain 0.1 to 10% by weight of the active ingredient compound. When the anti-bacterial composition is to be given orally, it is used in the form of a preparation such as tablets, capsules, powders, granules, dry syrups, liquids, syrups and the like, in association with a solid carrier or a liquid carrier as mentioned in the above.

For the capsules, tablets, granules and powders, in general, the proportion of the active ingredient compound present therein may be 3 to 99% by weight, preferably 5 to 90% by weight of the composition, with the balance being the carrier.

The dosage of the cephem compound of the formula (I) according to this invention to be used as the active ingredient, or its salt or ester depends on the age, body weight and symptoms of patients, and the purposes of the therapeutic treatment, and other factors. The dosage of the cephem compound is to give an effective amount of the cephem compound to combat against the infecting bacteria. The cephem compound at a necessary dosage may be administered continuously or intermittently as long as a total dosage of the cephem compound does not exceed a specific level which is decided in view of the results of animal tests and various circumstances.

When administered parenterally, the total dosage of the cephem compound of this invention is, of course, administered with appropriate adjustments being done in view of the way of administration, the conditions of patients such as age, body weight and sex, as well as foods and medicines concurrently administered. Suitable dosage and administration frequency of the cephem compound of this invention under given conditions must be determined by expert physician through the tests of determining optimal dosage of the cephem compound and in light of the above-mentioned guidelines. These requirements for the administration also applies to the oral administration of the cephem compound of this invention.

In another aspect of this invention, there is provided use of the cephem compound of the above formula (Ia) or the cephem compound of the above formula (Ib) or a pharmaceutically acceptable salt or ester thereof, in the preparation of an antibacterial agent.

BEST EMBODIMENT FOR WORKING OUT THE INVENTION

Next, processes the production of the compound of this invention having the formula (I) shown above are described. The cephem compound of this invention may be produced by different processes but may conveniently be produced either according to Production Process A which comprises step 1, step 2 and step 3 as depicted by the reaction equations shown in the following scheme, or according to Production Process B as stated hereinafter.

Production Process A

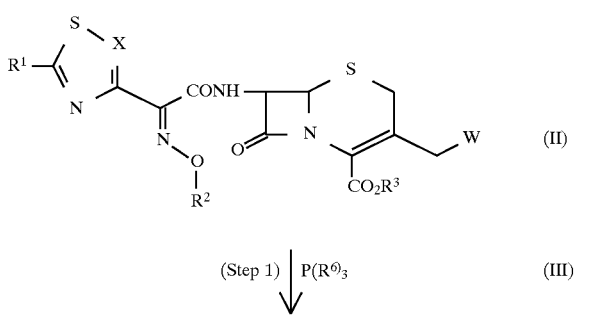

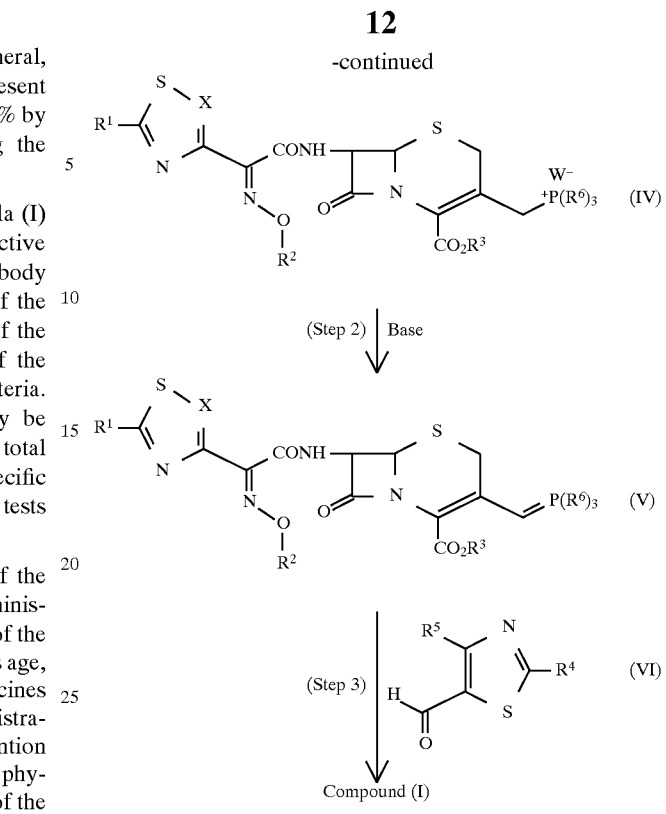

In the above reaction equations, X, $R^1$, $R^2$, $R^3$, $R^4$ and $R^5$ have the same meanings as defined hereinbefore, and $R^6$ denotes an aryl group such as phenyl group and W means a halogen atom.

Step 1

In this step, a compound of the general formula (II) or a salt thereof is reacted with a tri-substituted phosphine of the general formula (III). As an appropriate salt of the compound (II) may be used a salt of the compound (II) with such a base which is mentioned as examples of the base for forming the salt of the compound of formula (I) hereinbefore.

In this step, the reaction may desirably be carried out in the presence of a metal halide, including an alkali metal halide such as sodium iodide, potassium iodide, sodium bromide and the like. The reaction may be conducted in a solvent such as acetone, N,N-dimethylformamide, dimethylsulfoxide, methylene chloride, tetrahydrofuran and ethyl acetate, or mixed solvents of two or more of them. The reaction temperature is not critical but may desirably be room temperature. The compound having the general formula (IV) is produced as the reaction product, which may be isolated, if needed.

Step 2

In this step, the compound of the general formula (IV) or a salt thereof is reacted with a base. As a suitable salt of the compound (IV) may be used a salt of the compound (IV) with such a base which is mentioned as examples of the base for forming the salt of the compound (I). As the base which is used as the reactant, there may be mentioned an inorganic base which is an alkali metal hydrogen carbonate such as sodium hydrogen carbonate, potassium hydrogen carbonate or the like; an alkali metal carbonate such as sodium carbonate, potassium carbonate or the like; an alkaline earth metal carbonate such as calcium carbonate or the like, or a tri-(lower)alkylamine such as trimethylamine and triethylamine; pyridine; N-(lower)alkyl-morpholine; N,N-di-(lower)alkylbenzylamine and the like. In this step, the reaction may normally be carried out in acetone, tetrahydrofuran, methylene chloride or water, or mixed solvents of two or more of them. The reaction temperature is not critical but desirably is room temperature. The compound of the general formula (V) is produced as the reaction product, which may be isolated, if necessary.

Step 3

In this step, the compound of the general formula (V) or a salt thereof is reacted with an aldehyde of the general formula (VI) for the condensation reaction of these compounds. As the salt of the compound (V) may be used a salt of the compound (V) with such a base which is mentioned hereinbefore as the examples of the base available for forming the salt of the compound (I). In this step, the reaction may be carried out in methylene chloride, tetrahydrofuran or dioxane, or mixed solvents of two or more of them. The reaction temperature is not critical, but normally the reaction may be conducted under cooling or in the vicinity of room temperature. By this reaction, there is produced the target compound of the formula (I). Incidentally, the step 2 and the step 3 do not need to be conducted in the sequence mentioned above but may be conducted concurrently by reacting the compound (IV) with the aforesaid base and the aldehyde (VI) at the same time.

Production Process B

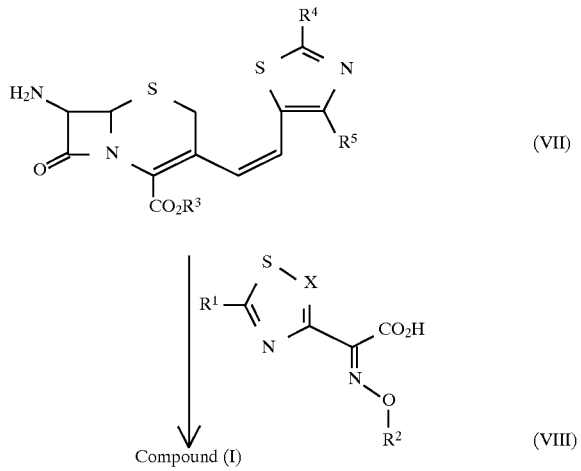

Compound (I)

In Production Process B, the compound of the formula (VII) where $R^3$, $R^4$ and $R^5$ are as defined above, or a reactive derivative at the amino group of the compound (VII), or a salt thereof is reacted with the compound of the formula (VIII) where X, $R^1$ and $R^2$ are as defined above, or a reactive derivative at the carboxyl group of the compound (VIII) or salt thereof, as shown in the above reaction equation.

Suitable examples of the reactive derivative at the amino group of the compound (VII), which may be used in the process of Production Process B, include such an imino derivative of the Shiff-base type which may be prepared by reaction of the compound (VII) with a carbonyl compound such as an aldehyde and a ketone; or such an enamine-type isomer which is a tautomer of said imino derivative; such a silyl derivative which may be prepared by reaction of the compound (VII) with a silyl compound such as bis-(trimethylsilyl)acetamide; and such a derivative which may be prepared by reaction of the compound (VII) with phosphorus trichloride or phosgene. Appropriate examples of the salts of the compound (VII) and the compound (VIII) include an acid addition salt thereof, for example, such an acid addition salt of the compound (VII) or (VIII) with an organic acid such as acetic acid, maleic acid, tartaric acid, benzenesulfonic acid, toluenesulfonic acid and the like; an acid addition salt of the compound (VII) or (VIII) with an inorganic acid such as hydrochloric acid, hydrobromic acid, sulfuric acid, phosphoric acid and the like; a metal salt of the compound (VII) or (VIII) with an alkali metal such as sodium and potassium or with an alkaline earth metal such as calcium and magnesium; ammonium salt of the compound (VII) or (VIII); and an amine salt of the compound (VII) of (VIII) with an organic amine such as triethylamine and dicyclohexylamine.

Suitable examples of the reactive derivative at the carboxyl group of the compound (VIII) include an acid halide, an acid azide, an acid anhydride, an activated amide and an activated ester of the compound (VIII). More especially, they may be an acid chloride or an acid bromide of the compound (VIII); or a mixed acid anhydride of the compound (VIII) formed with an acid, for example, with a substituted phosphoric acid such as dialkyl-phosphoric acid, dibenzyl-phosphoric acid, a halogenated phosphoric acid and the like, with a dialkyl phosphorous acid, with sulfurous acid, with thio-sulfuric acid, with sulfuric acid, with an alkyl carbonate such as methyl carbonate, ethyl carbonate and the like, with an aliphatic carboxylic acid such as pivalic acid, valeric acid, isovaleric acid, trichloroacetic acid and the like, or with an aromatic carboxylic acid such as benzoic acid and the like; or an activated amide of the compound (VIII) formed with imidazole, dimethylpyrazole, triazole or tetrazole, or an activated ester of the compound (VIII) such as cyanomethyl ester, methoxymethyl ester, vinyl ester, propargyl ester, p-nitrophenyl ester, 2,4-dinitrophenyl ester, trichlorophenyl ester, pentachloro-phenyl ester, mesylphenyl ester, phenylazophenyl ester, phenylthio ester, p-nitrophenylthio ester, p-cresylthio ester, carboxymethylthio ester, pyranyl ester, pyridyl ester and the like; or an ester of the compound (VIII) formed with a N-hydroxyl compound such as N,N-dimethyl-hydroxylamine, 1-hydroxy-2-(1H)-pyridone, N-hydroxy-succinimide, N-hydroxyphthalimide, 1-hydroxy-6-chloro-1H-benzotriazole and the like. These reactive derivatives of the compound (VIII) may properly be selected depending on the nature of the reactant (VII) to be used.

In the process of Production Process B, the reaction of condensing the compound (VII) with the compound (VIII) may usually be conducted in a conventional solvent such as water, acetone, dioxane, acetonitrile, chloroform, methylene chloride, tetrahydrofuran, ethyl acetate, N,N-dimethylformamide and pyridine, or in any other organic solvent which exerts no adverse effect on the progress of this reaction. These solvents may be used as a mixture with water.

In case when the compound (VIII) is used in the form of a free acid or in the form of a salt, the reaction may be conducted in the presence of a condensing agent. Examples of the condensing agent may be N,N'-dicyclohexylcarbodiimide; N-cyclohexyl-N'-morpholino-ethylcarbodiimide; N-cyclohexyl-N'-(4-diethylamino-cyclohexyl) carbodiimide; N,N'-diethylcarbodiimide; N,N'-diisopropyl-carbodiimide; N-ethyl-N'-(3-dimethylaminopropyl)carbodiimide: N,N'-carbonyl-bis(2-methylimidazole); penta-methyleneketene-N-cyclohexylimine; diphenylketene-N-cyclohexylimine; ethoxyacetylene; 1-alkoxy-1-chloroethylene; phosphorous acid trialkylester; ethyl polyphosphate; isopropyl polyphosphate; phosphorus oxychloride; phosphorus trichloride; thionyl chloride; triphenylphosphine; or Vilsmeier reagent which is prepared from reaction of N,N-dimethylformamide with thionyl chloride, phosgene and phosphorus oxychloride, and so on.

This reaction may also be conducted in the presence of an inorganic base or organic base. Examples of these inorganic and organic bases may be an alkali metal hydrogen carbonate such as sodium hydrogen carbonate, potassium hydrogen carbonate and the like, an alkali metal carbonate such as sodium carbonate, potassium carbonate and the like, or an alkaline earth metal carbonate such as calcium carbonate and the like, as well as a tri-(lower)alkyl amine such as trimethylamine and triethylamine, pyridine, N-(lower) alkylmorpholine, N,N-di-(lower)alkylbenzylamine and the like. The reaction temperature is not critical, but the reaction may usually be conducted under cooling or under heating. The target compound of the formula (I) is produced by the above reaction. The cephem compound of this invention having the general formula (I) and having the protected functional groups, which has been produced by the above described processes, may subsequently be subjected to further conventional step(s) for removal of the remaining protective groups therefrom, if needed.

The methods for removal of the carboxyl-protecting group or the amino-protecting group or the hydroxyimino-protecting group may suitably be chosen according to the nature of the protecting groups to be removed. The reaction for removal of the amino-protecting group may be achieved by hydrolysis or hydrogenolysis. To such N-protected cephem compound (I) having an acyl group as the amino-protecting group, there is applicable any conventional and optional deprotecting method, which includes a process comprising reacting the N-protected cephem compound with an imino-halogenating agent and then with an imino-etherifying agent and, if necessary,further subjecting the resultant reaction product to hydrolysis. The de-protecting method by hydrolysis with acid is one of the conventional methods useful for the removal of the amino-protecting group and may be applied to the removal of the amino-protecting groups such as alkoxycarbonyl group, formyl group and trityl group. The acid available for this purpose may properly be chosen from formic acid, trifluoroacetic acid, hydrochloric acid and the like, according to the nature of the amino-protecting group to be removed. The reaction for the removal of the amino-protecting group may be conducted in the absence of any solvent or in the presence of water or a hydrophilic organic solvent or mixed solvents of them. When tri-fluoroacetic acid is used for the acid hydrolysis, the reaction may be carried out in the presence of anisole. The reaction for removal of the carboxyl-protecting group may be achieved according to a conventional and optional method such as hydrolysis, reduction and other reactions. The deprotecting method by hydrolysis with acid is one of the conventional methods useful for the removal of the carboxyl-protecting group and may be applied to the removal of the carboxyl-protecting group such as a silyl group, diphenylmethyl group, p-methoxybenzyl group and the like. The lower alkoxy-lower alkoxy-lower alkyl group such as methoxyethoxymethyl group, which is employed to protect the hydroxyimino group, can be cleaved by treating with titanium tetrachloride in solution in methylene chloride.

When the cephem compound of the formula (I) as obtained from the above-mentioned processes is in the form of a free carboxylic acid, this compound may, if necessary, be converted into a metabolically unstable and non-toxic ester of the carboxyl group of the cephem compound. The method for this conversion into the metabolically unstable ester may be conducted by a conventional esterification process known per se, for example, by a process which comprises reacting the cephem compound as obtained in the free carboxylic acid form in solution in a solvent with a reactive derivative (for example, a halide such as iodide) of the ester-forming group to be introduced.

This invention is now further illustrated by the following Reference Example and Examples.

REFERENCE EXAMPLE 1

Production of 4-trifluoromethyl-5-thiazolaldehyde

A solution in toluene (25 ml) of 4-trifluoromethyl-5-thiazolcarboxylic acid ethyl ester (2000 mg) [see L. F. Lee et al., "J. Heterocycl. Chem.", 22, 1621 (1985)] was cooled to −75° C. and diisobutyl aluminium hydride (1.58 ml) was added dropwise thereto. After stirring the resulting mixture for 30 minutes at that temperature, water (3 ml) was added thereto and the temperature was raised to room temperature. An amount of 1N hydrochloric acid was added to said mixture under stirring, and then the resulting mixture was extracted with ethyl acetate three times. The organic layer so obtained was dried over anhydrous magnesium sulfate. When the dried organic layer was concentrated under a reduced pressure, followed by subsequent purification by silica gel column chromatography (eluent: hexane-ethyl acetate, 3:1) of the resultant concentrate, there was afforded the titled compound (0.30 mg; yield 19%).

NMR (CDC1): δ 9.14(1H, s), 10.29(1H, s)

EXAMPLE 1

Production of p-methoxybenzyl 7-[2-trityloxyimino-2-(2-tritylaminothiazol-4-yl)acetamido]-3-[2-(4-chloro-thiazol-5-yl)vinyl]-3-cephem-4-carboxylate (syn-isomer)(cis-isomer)(according to Production Process A)

To a solution in acetone (12 ml) of p-methoxybenzyl 7-[2-trityloxyimino-2-(2-tritylaminothiazol-4-yl)-acetamido]-3-chloromethyl-3-cephem-4-carboxylate (1532 mg) and triphenylphosphine (413 mg) was added sodium iodide (263 mg) at room temperature, and the resulting mixture was stirred for 2 hours.

The reaction solution obtained was concentrated to dryness under a reduced pressure and then methylene chloride (15 ml) was added to the residue. To the resulting solution was added 4-chloro-5-thiazolaldehyde (243 mg) (as disclosed in U.S. Pat. No. 4,839,350 specification), followed by adding a 5% aqueous sodium hydrogen carbonate (12.6 ml). After stirring at room temperature for 2 hours, the resultant reaction mixture was separated into an aqueous layer and an organic layer. The aqueous layer was extracted with methylene chloride. The extract so obtained was combined with the organic layer, and the resulting mixture was washed with a saturated aqueous sodium chloride, dried over anhydrous magnesium sulfate and then concentrated under a reduced pressure. The residue was purified by silica gel column chromatography (eluent: hexane-ethyl acetate, 3:2), to afford the titled compound (1266 mg; yield 76%).

NMR (CDCl$_3$): δ 3.04(1H, d, J=18.9 Hz) 3.43(1H,d,J= 18.9 Hz), 5.15(3H,m), 6.11(1H,m), 6.36(1H,d,J=12.8 Hz), 6.44(1H,m), 6.64(1H,d,J=12.8 Hz), 6.84(2H,m), 7.26(30H, m), 8.43(1H,s)

EXAMPLE 2

Production of 7-[2-hydroxyimino-2-(2-aminothiazol-4-yl)acetamido]-3-[2-(4-chlorothiazol-5-yl)vinyl]-3-cephem-4-carboxylic acid sodium salt (syn-isomer)(cis-isomer)

To a solution in anisole (1.5 ml) of p-methoxy-benzyl 7-[2-trityloxyimino-2-(2-tritylaminothiazol-4-yl)-acetamido]-3-[2-(4-chlorothiazol-5-yl)vinyl]-3-cephem-4- carboxylate (syn-isomer)(cis-isomer)(920 mg) as obtained in Example 1 and 4-methoxy-phenol (2050 mg) was added dropwise trifluoroacetic acid (7 ml) under ice-cooling. After stirring the resulting mixture for 1 hour under ice-cooling, pre-cooled isopropylether was added.

The precipitate so formed was recovered by filtration, washed with isopropyl ether, dried and then neutralized by reaction with a 5% aqueous sodium hydrogen carbonate. The neutralized solid was then purified by treating with a column of a non-ionic adsorptive resin, Diaion HP-20. Fractions of the eluate containing the desired product were collected, combined together, concentrated under a reduced pressure and then lyophilized to afford the titled compound (240 mg; yield 57%).

NMR (D$_2$O): δ 3.41(1H,d,J=18.5 Hz), 3.68(1H,d,J=18.5 Hz), 3.81(3H,s), 5.43(1H,d,J=4.8 Hz), 5.92(1H,d,J=4.8 Hz), 6.43(1H,d,J=11.5 Hz), 6.70(1H,d,J=11.5 Hz), 7.03(1H,s), 8.87(1H,s)

EXAMPLE 3

Production of 7-[2-hydroxyimino-2-(2-aminothiazol-4-yl)acetamido]-3-[2-(4-chlorothiazol-5-yl)vinyl]-3-cephem-4-carboxylic acid pivaloyloxymethyl ester (syn-isomer)(cis-isomer)

7-[2-Hydroxyimino-2-(2-aminothiazol-4-yl)acet-amido]-3-[2-(4-chlorothiazol-5-yl)vinyl]-3-cephem-4-carboxylic acid sodium salt (syn-isomer)(cis-isomer) (40 mg) as obtained in Example 2 was dissolved in N,N-dimethylformamide (1 ml). To the resulting solution was added iodomethyl pivalate (18.8 mg) under ice-cooling, and the mixture was stirred under the ice-cooling temperature for 1 hour.

The reaction solution obtained was diluted with ethyl acetate, washed with a small amount of ice water, dried over anhydrous magnesium sulfate and then concentrated under a reduced pressure to a volume of 0.15 ml. A pre-cooled isopropylether was added to the concentrate and the resultant precipitate was recovered by filtration, washed with isopropylether and dried to yield the titled compound (15 mg; yield 31%).

NMR (CDCl$_3$): δ 1.14(9H,s), 3.35(1H,d,J=18.0 Hz), 3.58 (1H,d,J=18.0 Hz), 5.18(1H,d,J=5.4 Hz), 5.77(1H,d,J=5.1 Hz), 5.85(1H,d,J=5.1 Hz), 5.98(1H,dd,J=5.4, 9.0 Hz), 6.45 (1H,d,J=11.7 Hz), 6.72(1H,d,J=11.7 Hz), 7.10(1H,br), 8.01 (1H,s) 8.65(1H,s), 10.78(1H,br)

EXAMPLE 4

Production of p-methoxybenzyl 7-[2-trityloxyimino-2-(2-tritylaminothiazol-4-yl)acetamido]-3-[2-(4-trifluoromethylthiazol-5-yl)vinyl]-3-cephem-4-carboxylate (syn-isomer)(cis-isomer)

The reaction and purification procedures of Example 1 were repeated using p-methoxybenzyl 7-[2-tri-tyloxyimino-2-(2-tritylaminothiazol-4-yl)acetamido]-3-chloromethyl-3-cephem-4-carboxylate (919 mg), triphenylphosphine (259 mg), sodium iodide (148 mg) and 4-tri-fluoromethyl-5-thiazolaldehyde (179 mg) as prepared in Reference Example 1. Thus, the titled compound (700 mg; yield 64%) was afforded.

NMR (CDCl$_3$): δ 2.98(1H,d,J=18.6 Hz), 3.14(1H,d,J= 18.6 Hz), 3.90(3H,s), 5.10(1H,d,J=4.9 Hz), 5.17(2H,s), 6.10 (1H,dd,J=9.2, 4.9 Hz), 6.43(1H,s), 6.53(1H,d,J=11.9 Hz), 6.88(3H,m), 7.06(1H,d,J=9.2 Hz), 7.29(33H,m), 8.48(1H,s)

EXAMPLE 5

Production of 7-[2-hydroxyimino-2-(2-aminothiazol-4-yl)acetamido]-3-[2-(trifluoromethylthiazol-5-yl)vinyl]-3-cephem-4-carboxylic acid sodium salt (syn-isomer) (cis-isomer)

The reaction and purification procedures of Example 2 were repeated using p-methoxybenzyl 7-[2-tri-tyloxyimino-2-(2-tritylaminothiazol-4-yl)acetamido]-3-[2-(4-trifluoromethylthiazol-5-yl)vinyl]-3-cephem-4-carboxylate (syn-isomer)(cis-isomer)(700 mg) as prepared in Example 4. Thus, the titled compound (166 mg; yield 53%) was obtained.

NMR (D$_2$O): δ 3.36(1H,d,J=17.9 Hz), 3.63(1H,d,J=17.9 Hz), 5.38(1H,d,J=4.9 Hz), 5.90(1H,d,4.9 Hz), 6.59(1H, d,J= 11.9 Hz), 6.86(1H,d,J=11.9 Hz), 6.99(1H,s), 8.94(1H,s)

EXAMPLE 6

Production of 7-[2-hydroxyimino-2-(2-aminothiazol-4-yl)acetamido]-3-[2-(4-trifluoromethylthiazol-5-yl)-vinyl]-cephem-4-carboxylic acid pivaloyloxymethyl ester (syn-isomer)(cis-isomer)

7-[2-Hydroxyimino-2-(2-aminothiazol-4-yl)acet-amido]-3-[2-(4-trifluoromethylthiazol-5-yl)vinyl]-3-cephem-4-carboxylic acid sodium salt (syn-isomer)(cis-isomer)(40 mg), which was obtained in Example 5, was used for the reaction with iodomethyl pivalate and subsequent purification in the same manner as in Example 3, to afford the titled compound (13 mg; yield 27%).

NMR (DMSO-d$_6$): δ 1.13(9H,s), 3.68(1H,d,J=18.0 Hz), 3.84(1H,d,J=18.0 Hz), 5.53(1H,d,J=5.1 Hz), 5.91(1H,d,J= 5.1 Hz), 5.98(1H,d,J=5.3 Hz), 6.17(1H,dd,J=5.3, 9.0 Hz), 6.88(1H,d,J=11.7 Hz), 7.07(1H,d,J=11.7 Hz), 7.40(1H,br), 9.44(1H,s) 9.80(1H,d,J=9.0 Hz), 11.6(1H,s)

EXAMPLE 7

Production of p-methoxybenzyl 7-[2-trityloxyimino-2-(2-tritylaminothiazol-4-yl)acetamido]-3-[2-(4-methyl-thiazol-5-yl)vinyl]-3-cephem-4-carboxylate (syn-isomer) (cis-isomer)(according to Production Process B)

To a solution in methylene chloride (15 ml) of 2-(2-tritylaminothiazol-4-yl)-2-trityloxyimioacetic acid (syn-isomer)(1000 mg), were added N,N-dicyclohexyl-carbodiimide (322 mg) and hydroxybenztriazole (211 mg) under ice-cooling. The resulting mixture was stirred at room temperatures for 3 hours. Then, there was added p-methoxybenzyl 7-amino-3-[2-(4-methylthiazol-5-yl)-vinyl]- 3-cephem-4-carboxylate (cis-isomer)(660 mg), and the mixture so obtained was allowed to stand at 5° C. for 12.5 hours. Insoluble matters were filtered off from the reaction solution and the filtrate was concentrated under a reduced pressure. The residue was purified by a silica gel column chromatography (eluent: hexane-ethyl acetate, 2:3), to yield the titled compound (1128 mg; yield 69%).

NMR (CDCl$_3$): δ 2.45(3H,s), 3.10(1H,d,J=18.4 Hz), 3.44 (1H,d,J=18.4 Hz), 3.83(3H,s), 5.15(3H,m), 6.11(1H,m), 6.32(1H,d,J=11.8 Hz), 6.44(1H,s), 6.56(1H,d,J=11.8 Hz), 6.83(3H,m), 7.30(33H,m), 8.49(1H,s)

EXAMPLE 8

Production of 7-[2-hydroxyimino-2-(2-aminothiazol-4-yl)acetamido]-3-[2-(4-methylthiazol-5-yl)vinyl]-3-cephem-4-carboxylic acid sodium salt (syn-isomer)(cis-isomer)

p-Methoxybenzyl 7-[2-trityloxyimino-2-(2-trityl-aminothiazol-4-yl)acetamido]-3-[2-(4-methylthiazol-5-yl)-vinyl]-3-cephem-4-carboxylate (syn-isomer)(cis-isomer) (1128 mg) as obtained in Example 7 was used for the reaction and subsequent purification in the same manner as in Example 2, to afford the titled compound (234 mg; yield 46%).

NMR (D$_2$O): δ 2.39(3H,s), 3.36(1H,d,J=17.9 Hz), 3.62 (1H,d,J=17.9 Hz), 5.40(1H,d,J=4.9 Hz), 5.89(1H,d,J=4.9 Hz), 6.32(1H,d,J=11.6 Hz), 6.68(1H,d,J=11.6 Hz), 7.00(1H, s), 8.79(1H,s)

EXAMPLE 9

Production of 7-[2-hydroxyimino-2-(2-aminothiazol-4-yl)acetamido]-3-[2-(4-methylthiazol-5-yl)vinyl]-3-cephem-4-carboxylic acid pivaloyloxymethyl ester (syn-isomer)(cis-isomer)

7-[2-hydroxyimino-2-(2-aminothiazol-4-yl)acetamido]-3-[2-(4-methylthiazol-5-yl)vinyl]-3-cephem-4-carboxylic acid sodium salt (syn-isomer)(cis-isomer)(40 mg) as obtained in Example 8 was used for the reaction with iodomethyl pivalate and subsequent purification in the same manner as in Example 3. Thus, the titled compound (13 mg); yield 27%) was obtained.

NMR (DMSO-$d_6$): δ 1.15(9H,s), 3.68(1H,d,J=18.0 Hz), 3.84(1H,d,J=18.0 Hz), 4.15(1H,d,J=5.3 Hz), 5.72(1H,d,J=5.1 Hz), 5.79(1H,d,J=5.1 Hz), 5.92(1H,dd,J=5.3, 9.0 Hz), 6.38(1H,d,J=11.5 Hz), 6.75(1H,d,J=11.5 Hz), 8.10(1H,br), 8.98(1H,s) 9.60(1H,d,J=9.0 Hz), 11.50(1H,s)

EXAMPLE 10

Production of p-methoxybenzyl 7-[2-trityloxyimino-2-(2-tritylaminothiazol-4-yl) acetamido]-3-[2-(thiazol-5-yl)vinyl]-3-cephem-4-carboxylate (syn-isomer) (cis-isomer and trans-isomer) (according to Production Process A)

The reaction similar to that of Example 1 was carried out using p-methoxybenzyl 7-[2-trityloxyimino-2-(2-tritylaminothiazol-4-yl)acetamido]-3-chloromethyl-3-cephem-4-carboxylate (1156 mg), triphenylphosphine (256 mg), sodium iodide (185 mg) and 5-thiazolaldehyde (640 mg). Purification was effected by silica gel column chromatography (eluent: toluene-ethyl acetate, 5:1), to afford cis-isomer (400 mg), trans-isomer (200 mg) and a mixture of cis- and trans-isomers (300 mg) of the titled compound (total yield: 93%).

Cis-isomer:

NMR (CDCl$_3$): δ 3.09(1H,d,J=18.6 Hz), 3.34(1H,d,J=18.6 Hz), 3.80(3H,s), 5.15(3H,m), 6.10(1H,dd,J=5.2, 9.0 Hz), 6.29(1H,d,J=11.8 Hz), 6.45(1H,s), 6.65(1H,d,J=11.8 Hz), 6.79(1H,br), 6.85(2H,d,J=8.8 Hz), 7.25(33H,m), 7.72 (1H,s), 8.58(1H,s)

Trans-isomer:

NMR (CDCl$_3$): δ 3.49(2H,s), 3,82(3H,s), 5.08(1H,d,J=4.9 Hz), 5.28(2H,s), 6.03(1H,dd,J=4.9, 8.8 Hz), 6.44(1H,s), 6.82(1H,d,J=8.8 Hz), 6.91(3H,m), 7.30(34H,m), 7.80(1H,s), 8.68(1H,s)

EXAMPLE 11

Production of 7-[2-hydroxyimino-2-(2-aminothiazol-4-yl)acetamido]-3-[2-(thiazol-5-yl)vinyl]-3-cephem-4-carboxylic acid sodium salt (syn-isomer) (cis-isomer)

The reaction and purification procedures of Example 2 were repeated using p-methoxybenzyl 7-[2-trityloxyimino-2-(2-tritylaminothiazol-4-yl)acetamido]-3-[2-(thiazol-5-yl)vinyl]-3-cephem-4-carboxylate (syn-isomer) (cis-isomer) (400 mg) as obtained in Example 10. Thus, the titled compound (120 mg; yield 68%) was obtained.

NMR (D$_2$O): δ 3.41(1H,d,J=18.3 Hz), 3.69(1H,d,J=18.3 Hz), 5.45(1H,d,J=4.8 Hz), 5.93(1H,d,J=4.8 Hz), 6.33(1H,d,J=11.5 Hz), 6.77(1H,d,J=11.5 Hz), 7.03(1H,s), 7.81(1H,s), 8.89(1H,s)

EXAMPLE 12

Production of 7-[2-hydroxyimino-2-(2-aminothiazol-4-yl)acetamido]-3-[2-thiazol-5-yl)vinyl]-3-cephem-4-carboxylic acid pivaloyloxymethyl ester (syn-isomer) (cis-isomer)

The procedures of Example 3 for the reaction with iodomethyl pivalate and the purification were repeated using 7-[2-hydroxyimino-2-(2-aminothiazol-4-yl)acetamido]-3-[2-(thiazol-5-yl)vinyl]-3-cephem-4-carboxylic acid sodium salt (syn-isomer)(cis-isomer)(22 mg) as obtained in Example 11. Thus, the titled compound (8 mg; yield 30%) was afforded.

NMR (DMSO-$d_6$): δ 1.14(9H,s), 3.66(1H,d,J=18.0 Hz), 3.85(1H,d,J=18.0 Hz), 5.38(1H,d,J=5.3 Hz), 5.68(1H,d,J=5.1 Hz), 5.74(1H,d,J=5.1 Hz), 5.90(1H,dd,J=5.3, 8.7 Hz), 6.32(1H,d,J=11.2 Hz), 6.71(1H,s), 6.82(1H,d,J=11.2 Hz), 7.95(1H,br), 9.05(1H,s) 9.65(1H,d,J=8.7 Hz)

EXAMPLE 13

Production of 7-[2-hydroxyimino-2-(2-aminothiazol-4-yl)acetamido]-3-[2-(thiazol-5-yl)vinyl]-3-cephem-4-carboxylic acid sodium salt (syn-isomer) (trans-isomer)

Reaction and purification similar to Example 2 were carried out using p-methoxybenzyl 7-[2-trityloxy-imino-2-(2-tritylaminothiazol-4-yl)acetamido]-3-[2-(thiazol-5-yl)vinyl]-3-cephem-4-carboxylate (syn-isomer) (trans-isomer) (200 mg) as obtained in Example 10. The titled compound (80 mg; yield 93%) was obtained.

NMR (D$_2$O): δ 3.70(1H,d,J=18.0 Hz), 3.75(1H,d,J=18.0 Hz), 5.29(1H,d,J=4.9 Hz), 5.87(1H,d,J=4.9 Hz), 6.91(1H,d,J=16.2 Hz), 6.98(1H,s), 7.12(1H,d,J=16.2 Hz), 7.80(1H,s), 8.81 (1H,s)

EXAMPLE 14

Production of 7-[2-hydroxyimino-2-(2-aminothiazol-4-yl)acetamido]-3-[2-(thiazol-5-yl)vinyl]-3-cephem-4-carboxylic acid pivaloyloxymethyl ester (syn-isomer) (trans-isomer)

Procedures of Example 3 for the reaction with iodomethyl pivalate and the purification were repeated using 7-[2-hydroxyimino-2-(2-aminothiazol-4-yl)acetamido]-3-[2-(thiazol-5-yl)vinyl]-3-cephem-4-carboxylic acid sodium salt (syn-isomer)(trans-isomer)(30 mg) as obtained in Example 13. Thus, the titled compound (12 mg; yield 34%) was obtained.

NMR (DMSO-$d_6$): δ 1.16(9H,s), 3.74(1H,d,J=18.5 Hz), 4.17(1H,d,J=18.5 Hz), 5.28(1H,d,J=5.2 Hz), 5.84(1H,dd,J=5.0, 8.7 Hz), 5.86(1H,d,J=5.4 Hz), 5.94(1H,d,J=5.4 Hz), 6.71(1H,s), 7.16(1H,d,J=16.4 Hz), 7.95(1H,br), 9.08(1H,s), 9.54(1H,d,J=8.7 Hz)

EXAMPLE 15

Production of p-methoxybenzyl 7-[2-methoxyethoxy-methyloxyimino-2-(5-tritylamino-1,2,4-thiadiazol-3-yl)-acetamido]-3-[2-(4-methylthiazol-5-yl)vinyl]-3-cephem-4-carboxylate(syn-isomer)(cis-isomer)(according to Production Process B)

To a solution in methylene chloride (20 ml) of 2-(5-tritylamino-1,2,4-thiadiazol-3-yl)-2-methoxyethoxy-methyloxyiminoacetic acid (syn-isomer)(900 mg) and 7-amino-3-[2-(4-methylthiazol-5-yl)vinyl]-3-cephem-4-carboxylic acid (cis-isomer)(827 mg), were added pyridine (0.63 ml) and phosphorus oxychloride (0.19 ml) in order at −20° C. The resulting mixture was stirred at the same temperature, −20° C., for 1 hour, and then ice water and methylene chloride were added thereto. After further stirring the mixture, the organic layer was separated. The organic layer obtained was washed with a saturated aqueous sodium chloride solution, dried over anhydrous magnesium sulfate and concentrated under a reduced pressure. The residue obtained was purified by silica gel column chromatography (eluent: hexane-ethyl acetate, 1:4), to afford the titled compound (1435 mg; yield 88%).

NMR (CDCl$_3$): δ 2.41(3H,s), 3.23(1H,d,J=18.2 Hz), 3.30 (3H,s), 3.47(1H,d,J=18.2 Hz), 3.54(2H,m), 3.80(3H,s), 3.91 (2H,m), 5.12(2H,s), 5.13(1H,d,J=4.8 Hz), 5.30(1H,d,J=7.5 Hz), 5.41(1H,d,J=7.5 Hz), 6.01(1H,dd,J=5.1, 8.4 Hz), 6.31 (1H,d,J=11.8 Hz), 6.58(1H,d,J=11.8 Hz), 6.82(2H,d,J=8.7 Hz), 7.28(17H,m), 7.48(1H,s), 8.05(1H,d,J=8.5 Hz), 8.56 (1H,s)

EXAMPLE 16

Production of 7-[2-hydroxyimino-2-(5-amino-1,2,4-thiadiazol-3-yl)acetamido]-3-[2-(4-methylthiazol-5-yl)-vinyl]-3-cephem-4-carboxylic acid sodium salt (syn-isomer) (cis-isomer)

To a solution in methylene chloride (10 ml) of p-methoxybenzyl 7-[2-methoxyethoxymethyloxyimino-2-(5-tritylamino-1,2,4-thiadiazol-3-yl)acetamido]-3-[2-(4-methylthiazol-5-yl)vinyl]-3-cephem-4-carboxylate(syn-isomer)(cis-isomer)(700 mg) obtained in Example 15, was added dropwise a methylene chloride solution (2.0 ml) of 1.0M titanium tetrachloride under ice-cooling, and the resulting mixture was stirred for 1.5 hours. Thus, the reaction of cleaving the methoxyethoxymethyl group was effected. A 5 ml portion of the reaction solution so obtained was taken and subjected to the reaction with the same reactant as in Example 2 and then to the purification similar to Example 2. Thus, the titled compound (35 mg) was obtained.

NMR (D$_2$O): δ 2.41(3H,s), 3.37(1H,d,J=18.2 Hz), 3.65 (1H,d,J=18.2 Hz), 5.41(1H,d,J=4.8 Hz), 5.94(1H,d,J=4.8 Hz), 6.34(1H,d,J=11.8 Hz), 6.69(1H,d,J=11.8 Hz), 8.83(1H, s)

INDUSTRIAL UTILIZABILITY

As described above, novel cephalosporin derivatives which exhibit high antibacterial activities against a variety of bacteria are obtained according to this invention. These cephalosporin derivatives are useful as antibacterial agent for therapeutical treatments of various bacterial infections.

We claim:

1. Syn-isomer of a cephem compound represented by the following formula (Ib)

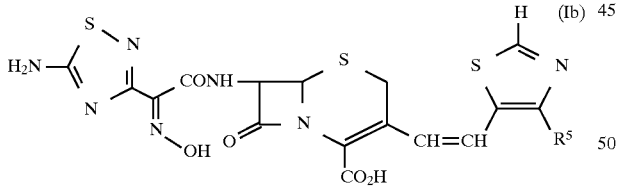

wherein R$^5$ stands for a hydrogen atom, a lower alkyl group, a halo-(lower)alkyl group or a halogen atom, or a pharmaceutically acceptable salt or ester at the 4-carboxyl group of said syn-isomer.

2. A compound according to claim 1, where the cephem compound of formula (Ib) or a salt or an ester thereof is:

7-[2-hydroxyimino-2-(5-amino-1,2,4-thiadiazol-3-yl)-acetamido]-3-[2-(4-chlorothiazol-5-yl)vinyl]-3-cephem-4-carboxylic acid (syn-isomer)(cis-isomer);

7-[2-hydroxyimino-2-(5-amino-1,2,4-thiadiazol-3-yl)-acetamido]-3-[2-(4-trifluoromethylthiazol-5-yl)vinyl]-3-cephem-4-carboxylic acid (syn-isomer)(cis-isomer);

7-[2-hydroxyimino-2-(5-amino-1,2,4-thiadiazol-3-yl)-acetamido]-3-[2-(4-methylthiazol-5-yl)vinyl]-3-cephem-4-carboxylic acid (syn-isomer)(cis-isomer);

7-[2-hydroxyimino-2-(5-amino-1,2,4-thiadiazol-3-yl)-acetamido]-3-[2-(thiazol-5-yl)vinyl]-3-cephem-4-carboxylic acid (syn-isomer)(cis-isomer); or sodium salt, pivaloyloxymethyl ester, acetoxymethyl ester, 1-acetoxyethyl ester, 1-(ethoxycarbonyloxy)ethyl ester, (2-oxo-1,3-dioxolen-4-yl)methyl ester or (5-methyl-2-oxo-1,3-dioxolen-4-yl)methyl ester of the above-mentioned cephem compounds.

3. 7-[2-Hydroxyimino-2-(2-aminothiazol-4-yl) acetamido]-3-[2-(4-chlorothiazol-5-yl)vinyl]-3-cephem-4-carboxylic acid (syn-isomer)(cis-isomer); or sodium salt, pivaloyloxymethyl ester, acetoxymethyl ester, 1-acetoxyethyl ester, 1-(ethoxycarbonyloxy)ethyl ester, (2-oxo-1,3-dioxolen-4-yl)methyl ester or (5-methyl-2-oxo-1,3-dioxolen-4-yl)methyl ester thereof.

4. 7-[2-Hydroxyimino-2-(2-aminothiazol-4-yl) acetamidol]-3-[2-(4-trifluoromethylthiazol-5-yl)vinyl]-3-cephem-4-carboxylic acid (syn-isomer)(cis-isomer); or sodium salt, pivaloyloxymethyl ester, acetoxymethyl ester, 1-acetoxyethyl ester, 1-(ethoxycarbonyloxy)ethyl ester, (2-oxo-1,3-dioxolen-4-yl)methyl ester or (5-methyl-2-oxo-1,3-dioxolen-4-yl)methyl ester thereof.

5. 7-[2-Hydroxyimino-2-(2-aminothiazol-4-yl) acetamido]-3-[2-(4-methylthiazol-5-yl)vinyl]-3-cephem-4-carboxylic acid (syn-isomer)(cis-isomer); or sodium salt, pivaloyloxymethyl ester, acetoxymethyl ester, 1-acetoxyethyl ester, 1-(ethoxycarbonyloxy)ethyl ester, (2-oxo-1,3-dioxolen-4-yl)methyl ester or (5-methyl-2-oxo-1,3-dioxolen-4-yl)methyl ester thereof.

6. 7-[2-Hydroxyimino-2-(2-aminothiazol-4-yl) acetamido]-3-[2-thiazol-5-yl)vinyl-3-cephem-4-carboxylic acid (syn-isomer)(cis-isomer); or sodium salt, pivaloyloxymethyl ester, acetoxymethyl ester, 1-acetoxyethyl ester, 1-(ethoxycarbonyloxy)ethyl ester, (2-oxo-1,3-dioxolen-4-yl)methyl ester or (5-methyl-2-oxo-1,3-dioxolen-4-yl)methyl ester thereof.

7. 7-[2-Hydroxyimino-2-(2-aminothiazol-4-yl) acetamido]-3-[2-(thiazol-5-yl)vinyl]-3-cephem-4-carboxylic acid (syn-isomer)(trans-isomer); or sodium salt, pivaloyloxymethyl ester, acetoxymethyl ester, 1-acetoxyethyl ester, 1-(ethoxycarbonyloxy)ethyl ester, (2-oxo-1,3-dioxolen-4-yl)methyl ester or (5-methyl-2-oxo-1,3-dioxolen-4-yl)methyl ester thereof.

8. An antibacterial composition, characterized in that the composition comprises as active ingredient at least one of the syn-isomer of a cephem compound represented by the following formula

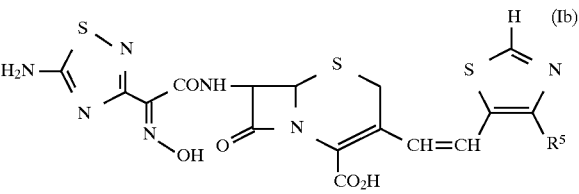

wherein R$^5$ is a hydrogen atom, a lower alkyl group, a halo-(lower)alkyl group or a halogen atom, or a pharmaceutically acceptable salt or ester at the 4-carboxyl group of said syn-isomer,in association with a pharmaceutically acceptable solid or liquid carrier.

* * * * *